United States Patent [19]

Hammond

[11] Patent Number: 5,344,819
[45] Date of Patent: * Sep. 6, 1994

[54] PHARMACEUTICAL COMPOSITIONS FOR USE IN TREATING INFLAMMATION

[75] Inventor: Geoffrey L. Hammond, Lambeth, Canada

[73] Assignee: Allelix Biopharmaceuticals Inc., Mississauga, Canada

[ * ] Notice: The portion of the term of this patent subsequent to Mar. 5, 2008 has been disclaimed.

[21] Appl. No.: 829,954

[22] Filed: Feb. 3, 1992

Related U.S. Application Data

[60] Continuation-in-part of Ser. No. 664,114, Mar. 4, 1991, Pat. No. 5,086,039, which is a division of Ser. No. 204,356, Jun. 9, 1988, Pat. No. 4,997,814, and a continuation-in-part of Ser. No. 653,736, Feb. 11, 1991, abandoned, which is a continuation of Ser. No. 204,400, Jun. 9, 1988, abandoned.

[51] Int. Cl.$^5$ .............................................. A61K 37/04
[52] U.S. Cl. .......................................... 514/8; 514/21; 514/179; 530/386
[58] Field of Search ............................. 514/8, 21, 179; 530/386

[56] References Cited

U.S. PATENT DOCUMENTS 4,997,814  3/1991  Hammond ................. 514/8
5,086,039  2/1992  Hammond ................. 514/8

Primary Examiner—Michael G. Wityshyn
Assistant Examiner—Choon Koh

[57] ABSTRACT

Inflammation in mammals is treated by administering anti-inflammatory agent complexed with corticosteroid binding globulin (CBG) that is produced by recombinant DNA-based techniques.

18 Claims, 3 Drawing Sheets

FIG. 1A

```
                         CAGCCTACCGCAGACTGGCCTGGCTATACTGGACA            35
     Met Pro Leu Leu Tyr Thr Cys Leu Leu Trp Leu Pro Thr Ser Gly Leu Trp Thr Val
-22  ATG CCA CTC CTC TAC ACC TGT CTT CTC TGG CTG CCC ACC AGC GGC CTC TGG ACC GTC   95
                              G
      -1      1
     Gln Ala Met Asp Pro Ala Ala Tyr Val Asn Met Ser Asn His His Arg Gly Leu Ala
-2   CAG GCC ATG GAT CCT GCT GCT TAT GTG AAC ATG AGT AAC CAT CAC CGG GGC CTG GCT  155
             NcoI

Ser Ala Asn Val Asp Phe Ala Phe Ser Leu Tyr Lys His Leu Val Ala Leu Ser Pro Lys
19   TCA GCC AAC GTT GAC TTT GCC TTC AGC CTG TAT AAG CAC CTA GCC TTG AGT CCC AAA  215

Lys Asn Ile Phe Ser Pro Val Ser Ile Ser Met Ala Leu Met Leu Ser Leu Gly
39   AAG AAC ATT TTC TCC CCT GTG AGC ATC TTA GCT ATG CTG TCC CTG GGC          275

Thr Cys Gly His Thr Arg Ala Gln Leu Leu Gln Gly Leu Phe Asn Leu Thr Glu Arg
59   ACC TGT GGC CAC ACA CGG GCC CAG CTT CTC CTG GGT TTC AAC CTC ACT GAG AGG      335

Ser Glu Thr Glu Ile His Gln Gly Phe Gln His Leu His Leu Gln Leu Ala Lys Ser Asp
79   TCT GAG ACT GAG ATC CAC CAG GGT TTC CAG CAC CTG CAA CTC CAG GCA AAG TCA GAC  395

Thr Ser Leu Glu Met Thr Met Gly Asn Ala Leu Asp Phe Leu Ser Gly Ser Leu Glu Leu Leu
99   ACC AGC TTA GAA ATG ACT ATG GGC AAT GCC TTG GAT TTT CTT GCC AGC CTG GAG TTG CTG   455

Glu Ser Phe Ser Ala Asp Ile Lys His Tyr Tyr Glu Val Leu Ala Met Asn Phe
119  GAG TCA TTC TCA GCA GAC ATC AAG CAC TAC TAT GAG GTC TTG GCT ATG AAT TTC     515

Gln Asp Trp Ala Thr Arg Gln Ile Asn Ser Tyr Val Lys Thr Gln Gly
139  CAG GAC TGG GCA ACA GCC AGA CAG ATC AAC AGC TAT GTC AAG AAT AAG ACA CAG GGG  575

Lys Ile Val Asp Leu Phe Ser Gly Leu Asp Ala Ile Leu Val Leu Asn Tyr
159  AAA ATT GTC GAC TTG TTT TCA GGG CTG GAT GCC ATC CTC CTG CTC AAC TAT         635

Ile Phe Phe Lys Gly Leu Thr Gln Pro Phe Asp Leu Ala Ser Thr Arg Glu Asn
179  ATC TTC TTC AAA GGC ACA CCC CAG TTT GAC GCA CTG AGC ACC AGG GAG AAC          695
```

```
|FROM FIG. 1A|                                                                                                                                          FROM FIG. 1A|
199 Phe Tyr Val Asp Glu Thr Thr Val Val Lys Val Pro Met Met Leu Gln Ser Ser Thr Ile
    TTC TAT GTG GAC GAG ACA ACT GTG GTG AAG GTG CCC ATG ATG TTG CAG TCG AGC ACC ATC   755
219 Ser Tyr Leu His Asp Ser Glu Leu Pro Cys Gln Leu Val Gln Met Asn Tyr Val Gly Asn
    AGT TAC CTT CAT GAC TCA GAG CTC CCC TGC CAG CTG GTG CAG ATG AAC TAC GTG GGC AAT   815
239 Gly Thr Val Phe Ile Leu Pro Asp Lys Gly Lys Met Asn Thr Val Ile Ala Ala Leu
    GGG ACT GTC TTC ATC CTT CCG GAC AAG GGG ATG AAC ACA GTC ATC GCT GCA CTG           875
259 Ser Arg Asp Ile Asn Arg Trp Ser Ala Gly Leu Thr Ser Ser Gln Val Asp Leu Tyr
    AGC CGG GAC ATT AAC AGG TGG TCC GCA GGC CTG ACC AGC AGC CAG GTG GAC CTG TAC       935
279 Ile Pro Lys Val Thr Ile Ser Gly Val Tyr Asp Leu Gly Asp Val Leu Glu Glu Met Gly
    ATT CCA AAG GTC ACC ATC TCT GGA GTC TAT GAC CTT GGA GAT GTG CTG GAG GAA ATG GGC   995
299 Ile Ala Asp Leu Phe Thr Asn Gln Ala Phe Ser Arg Ile Thr Gln Asp Ala Gln Leu
    ATT GCA GAC TTG TTC ACC AAC CAG GCA AAT TTC TCA CGC ATC ACC CAG GAC GCC CAG CTG   1055
319 Lys Ser Ser Lys Val His Lys Val Ala Leu Val Gln Leu Asn Glu Gly Val Asp Thr
    AAG TCA TCA AAG GTG CAT AAA GCT GTC CTA CAA CTC GAG GAG GGT GTG GAC ACA           1115
339 Ala Gly Ser Thr Gly Val Thr Leu Asn Leu Thr Ser Lys Pro Ile Ile Leu Arg Phe Asn
    GCT GGC TCC ACT GGG GTC ACC CTA AAC CTG ACG TCC AAG CCT ATC ATC TTG CGT TTC AAC   1175
359 Gln Pro Phe Ile Met Ile Phe Asp His Thr Trp Ser Ser Leu Phe Leu Ala Arg
    CAG CCC TTC ATC ATG ATC TTC GAC CAC ACC TGG AGC AGC CTT TTC CTG GCG AGG           1235
                383
379 Val Met Asn Pro Val
    GTT ATG AAC CCA GTG TAA GAGACCACCACCCAGAGCCTCAGCACTGTCTGACTTTGGGAACCAGGGATCCCA    1308
    CAGAAATGTTTTGGAGAGCGGAGGTTCCCCCAATCTCCTCCCAAGTTCTTCCCTCCAACCAGAGTTGTGTCTAACT      1387
    TTAGGCATCTTTTAATAAATGTCATTGCGACTCTGA 36                                           1458
```

PHARMACEUTICAL COMPOSITIONS FOR USE IN TREATING INFLAMMATION

CROSS REFERENCE TO RELATED APPLICATIONS

This application is a continuation-in-part of U.S. Ser. No. 07/664,114 filed Mar. 4, 1991 and incorporated herein by reference (now U.S. Pat. No. 5,086,039 issued Feb. 4, 1992) which is a divisional of U.S. Ser. No. 07/204,356 filed Jun. 9, 1988 (now U.S. Pat. No. 4,997,814 issued Mar. 5, 1991). This application is also a continuation-in-part of U.S. Ser. No. 07/653,736 filed Feb. 11, 1991 and incorporated herein by reference now abandoned, which is a continuation of U.S. Ser. No. 204,400 filed Jun. 9, 1988, now abandoned.

This invention relates to anti-inflammatory agents such as glucocorticoids and their use in treating inflammation.

BACKGROUND TO THE INVENTION

Glucocorticoids are steroid hormones, many of which are potent anti-inflammatory agents. Their physiological effects are not limited to their anti-inflammatory properties, however, nor are their effects restricted specifically to inflamed tissue. Protein, lipid and carbohydrate metabolism can be altered adversely and electrolyte balance can be disturbed particularly when large or repeated therapeutic doses of the anti-inflammatory glucocorticoids are administered.

Certain recently developed synthetic glucocorticoids show promise as therapeutic alternatives to the natural anti-inflammatory glucocorticoids such as cortisone, cortisol and corticosterone. The synthetic analogues, which include dexamethasone and betamethasone, exhibit reduced effects on electrolyte balance and tend therefore to elicit fewer adverse side effects. In many instances, they also exhibit greater potency as anti-inflammatory agents relative to their natural counterparts, presumably owing to their reduced binding affinity for the plasma protein known as corticosteroid binding globulin (CBG). It has been reported that natural glucocorticoids become biologically inactivated upon binding with CBG in the circulation whereas many synthetic glucocorticoids do not bind and thus remain active (see Mickelson et al., *Biochemistry* 1981, 20, 6211–6218 where binding affinities for some natural and synthetic glucocorticoids relative to CBG are tabled). The capacity of synthetic glucocorticoids to escape CBG-binding and thus to remain free and biologically active following administration is presumed to be at least partly responsible for their enhanced anti-inflammatory properties in vivo.

Apart from the numerous physiological effects exerted by glucocorticoids, their use in treating inflammation is further complicated by their ability to affect a broad range of tissues, whether inflamed or healthy. Because so many tissues are responsive to corticosteroids, they are rarely administered systemically unless inflammation is particularly severe or life threatening.

SUMMARY OF THE INVENTION

It is therefore an object of the present invention to provide a strategy useful therapeutically for localizing the effects of anti-inflammatory agents, such as the glucocorticoids, predominantly to a site of inflammation.

In accomplishing this object, there is provided, in accordance with one aspect of the invention, a pharmaceutical composition useful in treating inflammation in a mammal which comprises CBG, an anti-inflammatory agent which binds therewith, and a pharmaceutically acceptable carrier. Any anti-inflammatory agent which binds with appropriate affinity to CBG may be used in the present composition. Preferably, the anti-inflammatory agent is present in an amount sufficient to bind substantially all of the CBG present in the composition. In one preferred embodiment of the invention, the anti-inflammatory agent is a glucocorticoid. Generally, the amount of anti-inflammatory agent required in the present composition is less than that required in the absence of CBG since, as will be explained, CBG is capable of localizing the effects of the anti-inflammatory agent to an inflammation site.

In accordance with another aspect of the invention, there is provided a method for treating inflammation in a mammal which comprises administering thereto a pharmaceutical composition comprising CBG-bound anti-inflammatory agent. According to one embodiment of the invention, the CBG incorporated in the composition is recombinant human CBG.

BRIEF REFERENCE TO THE DRAWINGS

FIG. 1 illustrates the nucleotide sequence (SEQ ID NO:1) of a cDNA molecule isolated from a lambda gt11 human liver cDNA library, and the deduced amino acid sequence (SEQ ID No:2) of human CBG; and FIG. 2 illustrates the construction of an expression plasmid which incorporates human CBG-encoding DNA SEQ ID No:3 is also shown in this Figure.

DETAILED DESCRIPTION OF THE INVENTION

Figure 2:
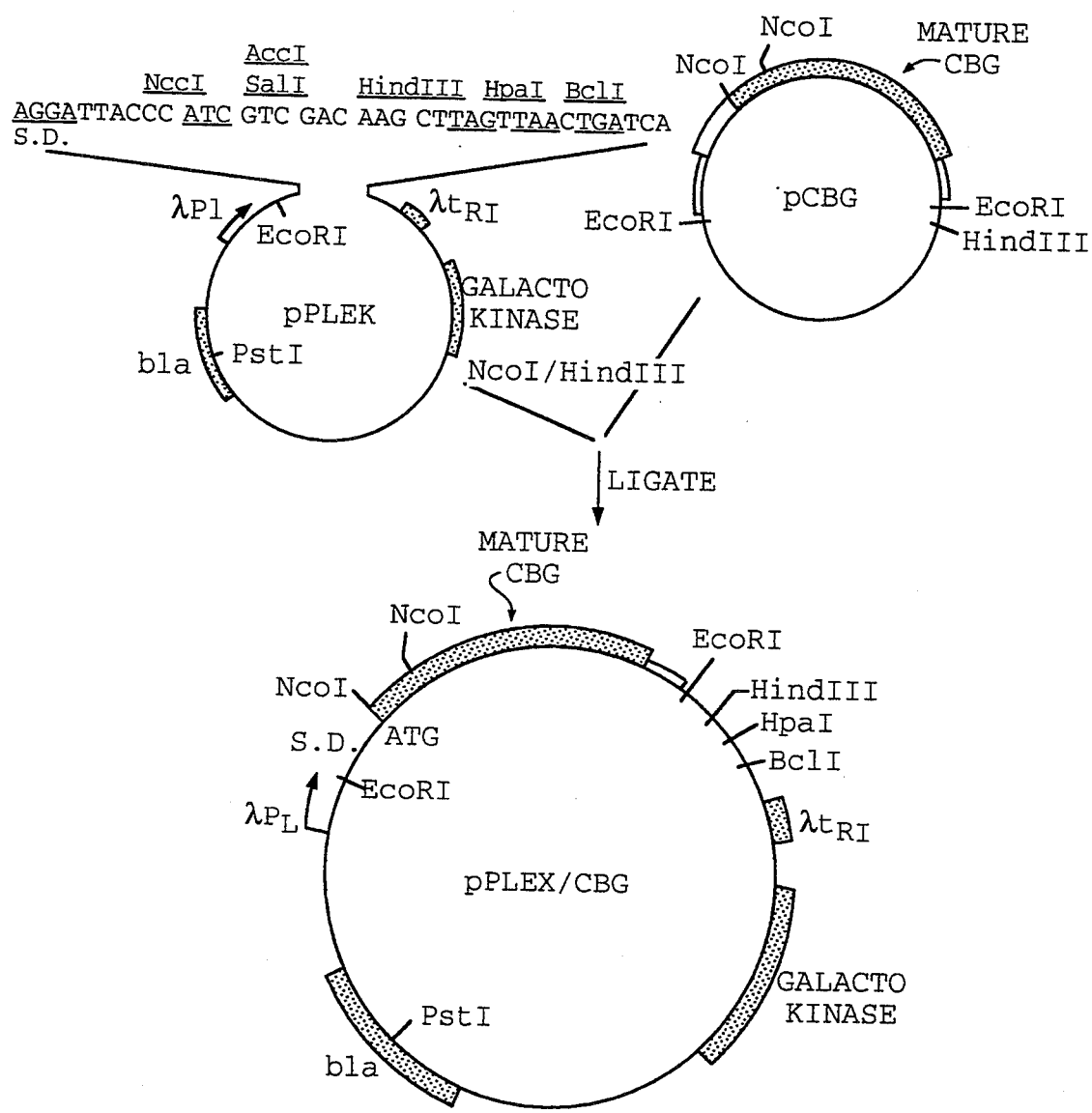

It has now been found that the binding affinity of CBG for such anti-inflammatory agents as the glucocorticoids can be exploited to improve upon their therapeutic effectiveness as anti-inflammatory agents even though such agents are rendered biologically inactive when bound by CBG. More particularly, it has been found that CBG-bound glucocorticoids can be released from CBG at local sites of inflammation by the action of leukocyte elastase, an enzyme which is prevalent at sites of inflammation. Leukocyte elastase specifically cleaves the CBG component of the glucocorticoid:CBG complex, allowing glucocorticoid to dissociate from CBG and exert its anti-inflammatory action directly at the inflammation site. Accordingly, administration of glucocorticoid in CBG-bound form is an effective means for localizing glucocorticoid effects to those tissues or sites at which inflammation is active, thus reducing the indiscriminate stimulation of other tissues by glucocorticoids which results in undesirable side effects. Similarly, any anti-inflammatory agent which binds with CBG can be targetted for release specifically at an inflammation site by administering that particular agent in CBG-bound form.

That CBG is cleaved specifically by leukocyte elastase, a serine protease released locally by neutrophils at sites of inflammation, is particularly remarkable. First, the region that contains the proposed elastase binding site on another elastase substrate, $\alpha_1$-antitrypsin, is not well conserved when compared with CBG. Moreover, again by analogy with $\alpha_1$-antitrypain, the putative elastase cleavage site on CBG involves a neighboring glycosylation site which is utilized in the CBG molecule, and is not involved in $\alpha_1$-antitrypsin. Yet, the experimental data herein provided demonstrates clearly that CBG is indeed cleaved by leucocyte elastase, at a site which is very close to that on the oxidized $\alpha_1$-antitrypsin molecule which is cleaved by macrophage elastase, and shows also that when cleaved by elastase, CBG loses steroid binding activity.

In accordance with the invention, anti-inflammatory agents which bind with CBG are administered in CBG-bound form to treat inflammation in mammals. It should be appreciated that the binding of a particular anti-inflammatory and CBG is mediated by the affinity of one molecule for the other and not through a physical link such as a covalent bond or chemical linking agent. The degree of affinity between CBG and the selected anti-inflammatory agent is desirably sufficient to enable CBG and the agent to remain in association following administration thereof to the mammal to be treated, and allow the corticosteroid to dissociate following elastase-induced cleavage of CBG at an inflammation site. To identify those anti-inflammatory agents suitable for use in the present invention, one simply determines whether CBG is capable of binding with a selected anti-inflammatory agent. In general, an anti-inflammatory agent having an affinity constant for CBG within the range from 0.1 to 10 nanomolar at about 4 C and physiological pH is preferred for use with CBG according to the present invention. A protocol for screening anti-inflammatory agents for suitability in the present context is described by Mickelson et al., supra, incorporated herein by reference, which allows the binding affinity of a selected steroid for CBG to be compared with the affinity of CBG for one of its natural ligands, cortisol. Any anti-inflammatory agent having CBG binding affinity which approximates that of cortisol is suitable for use in accordance with the present invention. Mickelson et al., supra, also identify some criteria useful in predicting whether a particular steroid will be capable of binding adequately with CBG, such as the presence of a 3-oxo group and the absence of an 11 $\alpha$-hydroxy group on the steroid. While these criteria can be useful in determining binding affinity of steroid for CBG, it should be understood that the determinative measure of suitability of anti-inflammatory agent, whether steroidal in structure or not, is ability of the agent to form a complex with CBG under the conditions noted above.

Specific anti-inflammatory agents useful herein include corticosteroids having glucocorticoid activity such as cortisol and other natural corticosteroids exhibiting anti-inflammatory properties such as corticosterone and cortisone. Synthetic glucocorticoids which exhibit reduced adverse effects on electrolyte balance, such as prednisolone and methylprednisolone are particularly suitable although, by intentional design, some other of the currently available synthetic glucocorticoids, such as dexamethasone, have an inappropriately low binding affinity for CBG. Nevertheless, synthetic corticosteroids developed subsequently or natural corticosteroids discovered hereafter are useful provided, of course, that they exhibit the appropriate level of anti-inflammatory activity and an appropriate CBG binding affinity, preferably a binding affinity for CBG which approximates that of cortisol (about 0.7 nanomolar at 4° C., physiological pH, as measured using the protocol described by Mickelson et al., supra).

The anti-inflammatory agent used in the pharmaceutical compositions of the invention should be of pharmaceutical grade. Whereas acid- and base-addition glucocorticoid salts are commonly employed in prior art compositions to enhance solubility of the glucocorticoid, in injectable solutions for example, salt forms of the selected glucocorticoid are not required in the present compositions although they may be used, if desired. When complexed with CBG, glucocorticoids are sufficiently soluble in solution in the amounts useful to treat inflammation, although solubilizers standard in the protein formulation art, such as mannitol, may be used.

CBG useful in the composition of the invention is now a well characterized protein, having been identified in human plasma over thirty years ago. It has since been identified in virtually every vertebrate species examined and has been isolated from numerous mammalian species including rabbit, guinea pig, rat, humans and others. Techniques for isolating CBG from serum are now well known in the art. The most practical and efficient of these techniques involve the use of affinity columns in which the immobilized ligand is either a glucocorticoid or a derivative thereof which binds with high affinity to CBG. The preparation of such a column in which a cortisol derivative is cross-linked on Sepharose and its use in isolating CBG are described by Rosner in *J. Steroid Biochem*, 1972, 3, 531–542. An improved method for purifying human CBG from pregnancy serum, in which CBG levels are about 2-fold higher than normal serum, is described by Robinson et al in *J. Endocr.* (1985) 104, 259–267, incorporated herein by reference. The procedure entails applying serum to a column in which the ligand is a corticosterone derivative, collecting the CBG-containing eluate and then subjecting the eluate to successive purification steps such as gel electrophoresis and including a step in which contaminating albumin is removed. Antibodies to CBG have also now been prepared (see Robinson et al., supra) and may also be employed to isolate CBG from serum.

As an alternative to using CBG that is serum-derived, the selected anti-inflammatory agent may be combined with CBG produced by application of established recombinant DNA-based techniques, if desired. For the purpose of producing such "recombinant CBG", there is further provided by the present invention an isolated DNA molecule which codes for human CBG. Those skilled in the art will appreciate that protocols and systems are now well established for genetically engineering organisms to produce desired proteins particularly for the bacteria such as *Escherichia coli* and *Bacillus subtilis*, fungi such as yeast and Aspergillus and for insect and mammalian cell hosts. Such techniques may similarly be applied for the purpose of expressing the human CBG-encoding DNA, in order to produce CBG for use in combination with anti-inflammatory ligand, in accordance with the present invention. The technique generally involves introducing into the host, DNA coding for the protein of interest linked operably with DNA enabling expression of the protein-encoding DNA by the host. Isolation of human CBG-encoding DNA, and its incorporation in a vector suitable for constructing a CBG-producing bacterial host, is described in the examples herein.

In general, provided that the CBG used in the composition has the appropriate binding affinity for the selected glucocorticoid and is susceptible to cleavage by elastase, such CBG is suitable. It is conceivable that elastase endogenous in the mammalian species to be treated may have some specificity for the CBG native to that species. Given the importance of CBG cleavage by elastase in the present context, it is recommended that the administered composition comprises CBG native to the mammalian species being treated. For example, human CBG is preferably used in compositions administered to treat inflammation in humans and equine CBG is used when horses are to be treated.

To prepare compositions of the invention, the selected anti-inflammatory agent and CBG are simply admixed in solution, such as physiological saline, at pH 7.5, with agitation to generate the required complexes. Formation of CBG:anti-inflammatory agent complexes can be facilitated by incubating at physiological temperature and pH. It is important, when CBG-bound glucocorticoids are prepared to maintain pH above 6 because the affinity of CBG for glucocorticoid is reduced below pH 6. It is desirable, in order to achieve the maximum localizing effect of CBG, that the CBG in the administered composition is saturated with glucocorticoid i.e. the molar ratio of glucocorticoid bound to CBG in the composition is substantially 1:1. To accomplish this, it is preferred to use a molar excess i.e. a stoichiometric excess, of glucocorticoid such as a molar ratio of 2:1 (glucocorticoid:CBG) or greater, when generating the complexed material. Unbound glucocorticoid may remain with the complexed material, if desired.

To formulate CBG-bound glucocorticoid for administration, any of the conventional pharmaceutically acceptable carriers may be used, selection of which depends on the intended mode of administration and is dictated to some extent by the proteinaceous nature of the complexes. Injectable solutions may be prepared using well known liquid vehicles such as buffered saline and physiological saline. Compositions for topical application may be prepared as creams, lotions or ointments using an appropriate base such as triglycerides. Surface active agents may also be used as may preservatives to prevent microbial growth over prolonged storage periods. Aerosol inhalable formulations of CBG-bound glucocorticoid may also be prepared using propellant and an appropriate liquid vehicle.

The compositions of the invention are useful in pharmaceutical and in veterinary applications to treat a variety of conditions involving inflammation. It will be appreciated that the compositions are particularly better adapted for systemic administration than known compositions comprising free anti-inflammatory agent since CBG-binding thereof is capable, by the limiting of therapeutic action to an inflammation site, of reducing the potential for adverse side effects elsewhere in the body. Because of the effect which CBG has on controlling release of glucocorticoid, for example, it may be used in the present compositions in lower amounts relative to compositions of glucocorticoid per se, to elicit an anti-inflammatory response. When administered systemically as an injectable solution, formulations will comprise glucocorticoid (as CBG-bound glucocorticoid) in a molar range of 5–500 μM. To determine appropriate unit doses for treating a specific medical conditions with a particular anti-inflammatory agent, reference may be made to product monographs or more generally to Pharmacopoeias, such as Martindale, *The Extra Pharmacopoeia* Ed, J. E. F. Reynolds, The Pharmaceutical Press, London, 1982 (see particularly pp 446–485).

The compositions of the invention are useful to treat the same inflammation-related medical conditions or disorders as are treatable by the anti-inflammatory agents per se. In this connection, reference may be made to *The Extra Pharmacopoeia* cited above and incorporated herein by reference. For example, administration systemically of CBG-bound anti-inflammatory agent will be useful to treat blood disorders including autoimmune haemolytic anemia, idiopathic thrombocytopenic purpura, arthritis, septicemia etc. Local injection may be appropriate to treat collagen and rheumatoid disorders as well as certain connective tissue disorders. In cream, ointment or lotion form, the compositions may be applied to treat inflammation active at exposed areas of the skin. Topical administration of the compositions may be applied to open wounds to reduce inflammation. The administration of aerosols is appropriate for treating adult respiratory distress syndrome, respiratory ailments such as steroid dependent asthma and interstital lung disease. In general, administration of the compositions of the invention will be useful to reduce inflammation in areas where the CBG-corticosteroid complexes can become exposed, following administration, to the action of elastase.

Demonstration that Leucocyte Elastase Cleaves CBG

Human CBG was purified by affinity chromatography and Blue Sepharose chromatography, as previously described (Robinson et al., (1985) J. Endocrinol. 104:250). To evaluate the relationship of CBG to serine proteases, approximately 1 μg pure CBG was incubated (5 min at 37° C.) in 30 mM Tris, pH 7.5 (or pH optimal appropriate for the different serine proteases), with 20 ng human leucocyte elastase (Elastin Products Company, Inc), cathepsin G (EPC), thrombin (Boehringer Mannheim Canada) or plasmin (BMC). The reaction was terminated by boiling in 5 μl SDS-PAGE loading buffer, and then subjected to electrophoresis on a 12%-SDS polyacrylamide gel. After the gel was stained with Coomasie Blue, it was apparent that, under the experimental conditions, a clear ~5 kDa reduction in the apparent $M_r$ of human CBG occurred only after incubation with elastase.

In order to determine the site of cleavage, CBG and elastase were again incubated under the same conditions. The reaction was "snap frozen" and stored at −70° C. until subjected to amino-terminal sequence analysis. The results revealed two CBG fragments: the authentic amino-terminus of mature human CBG, (Fernlund and Laurell (1981) J. Steroid Biochem. 14:545), together with a second sequence which was identified as starting with residue 342 (Thr) in the mature form of human CBG (Hammond et al. (1987) Proc. Natl. Acad. Sci. USA 84:5153).

The steroid binding properties of human CBG were also tested using a cortisol binding capacity assay (Hammond and Lahteenmaki (1982) Clin. Chem. Acta 132:101) before and after a standard incubation with elastase, as described above. In this way it could be shown that >95% of the steroid binding activity of human CBG was lost after treatment with elastase, indicating that CBG had lost its binding affinity for the anti-inflammatory agent cortisol following exposure to elastase.

Isolation of CBG-encoding cDNA

One of three human liver cDNA clones previously isolated as described by Hammond et al in "Binding Proteins of Steroid Hormones", Editions INSERM-/John Libbey Eurotext, Ltd, 1986, 149:113, incorporated herein by reference, was radiolabelled ($^{32}$P-labelled dCTP) and the same library re-screened therewith to isolate a full length CBG cDNA. Nitrocellulose filters (Schleicher and Schuell; BA85, 0.45 μm pore size) were used to transfer DNA and were hybridized with $2 \times 10^6$ dpm of the CBG cDNA probe per ml, in the presence of 50% (vol/vol) formamide at 42 C. Blots were washed three times for 5 min at room temperature in 0.3M NaCl/0.03M sodium citrate (2×SSC), once for 30 min in 1×SSC at 42° C. Filters were autoradiographed for 24 hr with Kodak XR-5 film at −80° C. with a Dupont Cronex Hi-Plus intensifying screen. The largest CBG cDNA isolated in this way was subsequently sub-cloned into pBR322 for restriction mapping and the production of restriction fragments which fragments were subcloned further into M13mp18 and M13mp19 bacteriophage vectors for the production of single-stranded templates which were then sequenced by the dideoxy chain-termination method. The same probe was used to screen a lambda gt11 library of human lung cDNA and a clone isolated in this manner was also sequenced as just described.

The nucleotide sequence (SEQ ID No:1) of the isolated human liver cDNA is represented in FIG. 1 together with the amino acid sequence (SEQ ID No:2) coded by the longest open reading. The same nucleotide sequence was found in the isolated lung cDNA molecule except that the isolated cDNA did not extend beyond residue $-18$ and that the 54th nucleotide is "G" rather than "A" as in the liver cDNA.

As noted in FIG. 1, the longest open reading frame codes for a peptide of 405 amino acids that starts at an initiation codon 35 nucleotides from the 5' end of the molecule and ends with a TAA termination codon located 169 nucleotides before the polyadenylation site. The eight residue NH$_2$-terminal sequence suggested previously by Fernlund, supra, is located between residues 23 and 31. The preceding 22 amino acids are predominantly hydrophobic in character and serve as a signal peptide that is cleaved during production of the mature peptide. Accordingly, as defined herein, mature human CBG i.e. that form of the molecule which circulates in plasma, is a 383 amino acid polypeptide which comprises the amino acid sequence from Met$^{+1}$ to Val$^{383}$ inclusive. The calculated molecular weight of the molecule, in unglycosylated form, is 42,646 which agrees with previous estimates. Two cysteine residues are contained in the molecule at positions 60 and 228. There are also six consensus sequences for the possible attachment of N-linked oligosaccharide chains at the positions indicated by the symbol "•". Notably, the ninth residue from the N-terminus is likely glycosylated which could explain previous difficulties encountered in sequencing beyond residue eight using pure protein. Deduction of the amino acid sequence form a corresponding DNA sequence has avoided this difficulty.

As note previously herein, to enable production of recombinant human CBG is first linked operably into any suitable expression vector. For expression in *E. coli*, for example, the expression vector pPLEX was employed. In particular, the isolated cDNA molecule, having the DNA sequence illustrated in FIG. 1 (SEQ ID No:1), was cloned into the EcoRI site of a convention plasmid using EcoRI linkers to generate pCBG as shown in FIG. 1. Of significance in the cloning procedure outline below is the availability of an NcoI site inherent in the cDNA molecule at the initiation codon of the mature CBG coding region (see FIG. 1, SEQ ID No:1) and the availability of a unique HindIII site downstream of the termination codon. As shown in FIG. 2 (SEQ ID No:3), plasmid pPLEX (described by Sczakiel et al. in *Nucleic Acids Research*, 1987, 15(4):1878) is well suited to receive an NcoI/HindIII fragment from pCBG. Plasmid pPLEX has an NcoI site available immediately downstream of the ribosome binding site and a P$_L$ promoter and a HindIII site which is 3' of the NcoI site.

Although the NcoI site at the initiation codon of the CBG cDNA is not unique (a second NcoI site is present in the CBG coding region) controlled digestion and isolation enabled isolation of the entire mature CBG coding region as a NcoI/HindIII fragment which was cloned into the pPLEX plasmid following NcoI and HindIII digestion, to generate pPLEX/CBG as shown in FIG. 2. Significantly, pPLEX/CBG comprises DNA coding for mature CBG linked directly with DNA enabling expression thereof in *E. coli*.

*E. coli* cells, such as strain NF-1, can be transformed with pPLEX/CBG using conventional technology and cultured under conditions suitable for activating the P$_L$ promoter contained on the plasmid. Mature CBG expressed by the transformants may be recovered from the cell lysate using an affinity column which employs a steroid analogue which binds CBG, as an immobilized ligand e.g. as described by Hammond et al. in *J. Endocrinol* (1985) 104, 259–267.

We claim:

1. A pharmaceutical composition useful in treating inflammation in a mammal, said composition comprising CBG, an anti-inflammatory agent having an affinity constant for CBG between 0.1 and 10 nM at about 4° C. and physiological pH, and a pharmaceutically acceptable carrier, wherein said CBG is recombinant human CBG.

2. The composition according to claim 1 wherein the CBG is present in an amount sufficient to bind substantially all of the anti-inflammatory agent in the composition.

3. The composition according to claim 1 wherein said anti-inflammatory agent is a glucocorticoid.

4. The composition according to claim 3, wherein said glucocorticoid is selected from cortisol, prednisolone and methylprednisolone.

5. The composition according to claim 1 which is an injectable solution.

6. The composition according to claim 1 in a form suitable for topical administration.

7. The composition according to claim 6 which is an aerosol.

8. A method for treating inflammation in a human patient, comprising the step of administering to the patient a pharmaceutical composition comprising CBG, an anti-inflammatory agent having an affinity constant for CBG between 0.1 and 10 nM at about 4° C. and physiological pH, and a pharmaceutically acceptable carrier, wherein said CBG is recombinant human CBG.

9. The method according to claim 8 wherein said anti-inflammatory agent is a glucocorticoid.

10. The method according to claim 9 wherein said anti-inflammatory agent is selected from cortisol, prednisolone and methylprednisolone.

11. The method according to claim 8 wherein said composition is administered by injection.

12. The method according to claim 8 wherein said composition is administered topically.

13. The method according to claim 8 wherein said composition is administered by inhalation.

14. A pharmaceutical composition comprising recombinant human CBG, a stoichiometric excess of cortisol, and a pharmaceutically acceptable carrier.

15. A composition as claimed in claim 1, wherein said recombinant CBG is produced in a bacterial cell.

16. A composition as claimed in claim 1, wherein said recombinant CBG is produced in *E. coli*.

17. A composition as claimed in claim 1, wherein said recombinant CBG is produced in a fungal cell.

18. A composition as claimed in claim 1, wherein said recombinant CBG is produced in a yeast cell.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1423 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 36..1253

( i x ) FEATURE:
        ( A ) NAME/KEY: sigpeptide
        ( B ) LOCATION: 36..101

5,344,819

-continued (ix) FEATURE:
(A) NAME/KEY: matpeptide
(B) LOCATION: 102..1253

(xi) SEQUENCE DESCRIPTION: SEQ ID NO:1:

```
CAGCCTACCG CAGACTGGCC TGGCTATACT GGACA ATG CCA CTC CTC CTC TAC                53
                                       Met Pro Leu Leu Leu Tyr
                                       -22          -20

ACC TGT CTT CTC TGG CTG CCC ACC AGC GGC CTC TGG ACC GTC CAG GCC              101
Thr Cys Leu Leu Trp Leu Pro Thr Ser Gly Leu Trp Thr Val Gln Ala
    -15              -10                          -5

ATG GAT CCT AAC GCT GCT TAT GTG AAC ATG AGT AAC CAT CAC CGG GGC              149
Met Asp Pro Asn Ala Ala Tyr Val Asn Met Ser Asn His His Arg Gly
 1               5                  10                  15

CTG GCT TCA GCC AAC GTT GAC TTT GCC TTC AGC CTG TAT AAG CAC CTA              197
Leu Ala Ser Ala Asn Val Asp Phe Ala Phe Ser Leu Tyr Lys His Leu
             20                  25                  30

GTG GCC TTG AGT CCC AAA AAG AAC ATT TTC ATC TCC CCT GTG AGC ATC              245
Val Ala Leu Ser Pro Lys Lys Asn Ile Phe Ile Ser Pro Val Ser Ile
         35                  40                  45

TCC ATG GCC TTA GCT ATG CTG TCC CTG GGC ACC TGT GGC CAC ACA CGG              293
Ser Met Ala Leu Ala Met Leu Ser Leu Gly Thr Cys Gly His Thr Arg
     50                  55                  60

GCC CAG CTT CTC CAG GGC CTG GGT TTC AAC CTC ACT GAG AGG TCT GAG              341
Ala Gln Leu Leu Gln Gly Leu Gly Phe Asn Leu Thr Glu Arg Ser Glu
 65                  70                  75                  80

ACT GAG ATC CAC CAG GGT TTC CAG CAC CTG CAC CAA CTC TTT GCA AAG              389
Thr Glu Ile His Gln Gly Phe Gln His Leu His Gln Leu Phe Ala Lys
                 85                  90                  95

TCA GAC ACC AGC TTA GAA ATG ACT ATG GGC AAT GCC TTG TTT CTT GAT              437
Ser Asp Thr Ser Leu Glu Met Thr Met Gly Asn Ala Leu Phe Leu Asp
             100                 105                 110

GGC AGC CTG GAG TTG CTG GAG TCA TTC TCA GCA GAC ATC AAG CAC TAC              485
Gly Ser Leu Glu Leu Leu Glu Ser Phe Ser Ala Asp Ile Lys His Tyr
         115                 120                 125

TAT GAG TCA GAG GTC TTG GCT ATG AAT TTC CAG GAC TGG GCA ACA GCC              533
Tyr Glu Ser Glu Val Leu Ala Met Asn Phe Gln Asp Trp Ala Thr Ala
     130                 135                 140

AGC AGA CAG ATC AAC AGC TAT GTC AAG AAT AAG ACA CAG GGG AAA ATT              581
Ser Arg Gln Ile Asn Ser Tyr Val Lys Asn Lys Thr Gln Gly Lys Ile
145                 150                 155                 160

GTC GAC TTG TTT TCA GGG CTG GAT AGC CCA GCC ATC CTC GTC CTG GTC              629
Val Asp Leu Phe Ser Gly Leu Asp Ser Pro Ala Ile Leu Val Leu Val
                 165                 170                 175

AAC TAT ATC TTC TTC AAA GGC ACA TGG ACA CAG CCC TTT GAC CTG GCA              677
Asn Tyr Ile Phe Phe Lys Gly Thr Trp Thr Gln Pro Phe Asp Leu Ala
             180                 185                 190

AGC ACC AGG GAG GAG AAC TTC TAT GTG GAC GAG ACA ACT GTG GTG AAG              725
Ser Thr Arg Glu Glu Asn Phe Tyr Val Asp Glu Thr Thr Val Val Lys
         195                 200                 205

GTG CCC ATG ATG TTG CAG TCG AGC ACC ATC AGT TAC CTT CAT GAC TCA              773
Val Pro Met Met Leu Gln Ser Ser Thr Ile Ser Tyr Leu His Asp Ser
     210                 215                 220

GAG CTC CCC TGC CAG CTG GTG CAG ATG AAC TAC GTG GGC AAT GGG ACT              821
Glu Leu Pro Cys Gln Leu Val Gln Met Asn Tyr Val Gly Asn Gly Thr
225                 230                 235                 240

GTC TTC TTC ATC CTT CCG GAC AAG GGG AAG ATG AAC ACA GTC ATC GCT              869
Val Phe Phe Ile Leu Pro Asp Lys Gly Lys Met Asn Thr Val Ile Ala
                 245                 250                 255

GCA CTG AGC CGG GAC ACG ATT AAC AGG TGG TCC GCA GGC CTG ACC AGC              917
Ala Leu Ser Arg Asp Thr Ile Asn Arg Trp Ser Ala Gly Leu Thr Ser
             260                 265                 270
```

-continued

| | | | | | | | | | | | | | | | | |
|---|---|---|---|---|---|---|---|---|---|---|---|---|---|---|---|---|
| AGC | CAG | GTG | GAC | CTG | TAC | ATT | CCA | AAG | GTC | ACC | ATC | TCT | GGA | GTC | TAT | 965 |
| Ser | Gln | Val | Asp | Leu | Tyr | Ile | Pro | Lys | Val | Thr | Ile | Ser | Gly | Val | Tyr | |
| | | 275 | | | | | 280 | | | | | 285 | | | | |
| GAC | CTT | GGA | GAT | GTG | CTG | GAG | GAA | ATG | GGC | ATT | GCA | GAC | TTG | TTC | ACC | 1013 |
| Asp | Leu | Gly | Asp | Val | Leu | Glu | Glu | Met | Gly | Ile | Ala | Asp | Leu | Phe | Thr | |
| | | 290 | | | | 295 | | | | | 300 | | | | | |
| AAC | CAG | GCA | AAT | TTC | TCA | CGC | ATC | ACC | CAG | GAC | GCC | CAG | CTG | AAG | TCA | 1061 |
| Asn | Gln | Ala | Asn | Phe | Ser | Arg | Ile | Thr | Gln | Asp | Ala | Gln | Leu | Lys | Ser | |
| 305 | | | | | 310 | | | | | 315 | | | | | 320 | |
| TCA | AAG | GTG | GTC | CAT | AAA | GCT | GTG | CTG | CAA | CTC | AAT | GAG | GAG | GGT | GTG | 1109 |
| Ser | Lys | Val | Val | His | Lys | Ala | Val | Leu | Gln | Leu | Asn | Glu | Glu | Gly | Val | |
| | | | | 325 | | | | | 330 | | | | | 335 | | |
| GAC | ACA | GCT | GGC | TCC | ACT | GGG | GTC | ACC | CTA | AAC | CTG | ACG | TCC | AAG | CCT | 1157 |
| Asp | Thr | Ala | Gly | Ser | Thr | Gly | Val | Thr | Leu | Asn | Leu | Thr | Ser | Lys | Pro | |
| | | | 340 | | | | | 345 | | | | | 350 | | | |
| ATC | ATC | TTG | CGT | TTC | AAC | CAG | CCC | TTC | ATC | ATC | ATG | ATC | TTC | GAC | CAC | 1205 |
| Ile | Ile | Leu | Arg | Phe | Asn | Gln | Pro | Phe | Ile | Ile | Met | Ile | Phe | Asp | His | |
| | | | 355 | | | | | 360 | | | | | 365 | | | |
| TTC | ACC | TGG | AGC | AGC | CTT | TTC | CTG | GCG | AGG | GTT | ATG | AAC | CCA | GTG | TAAGAGAC | 1260 |
| Phe | Thr | Trp | Ser | Ser | Leu | Phe | Leu | Ala | Arg | Val | Met | Asn | Pro | Val | | |
| | | 370 | | | | 375 | | | | | 380 | | | | | |

CCCACCCAGA GCCTCAGCAC TGTCTGACTT TGGGAACCAG GGATCCCACA GAAATGTTTT 1320

GGAGAGCGGG AGGTTTCCCC CAATCTCCTC CAAGTTCTTC TCCCTCCAAC CAGAGTTGTG 1380

TCTAACTTTA GGCATCTTTT AATAAATGTC ATTGCGACTC TGA 1423

( 2 ) INFORMATION FOR SEQ ID NO:2:

( i ) SEQUENCE CHARACTERISTICS:
        ( A ) LENGTH: 405 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Pro | Leu | Leu | Leu | Tyr | Thr | Cys | Leu | Leu | Trp | Leu | Pro | Thr | Ser | Gly |
| -22 | | -20 | | | | | -15 | | | | | -10 | | | |
| Leu | Trp | Thr | Val | Gln | Ala | Met | Asp | Pro | Asn | Ala | Ala | Tyr | Val | Asn | Met |
| | -5 | | | | | 1 | | | | 5 | | | | | 10 |
| Ser | Asn | His | His | Arg | Gly | Leu | Ala | Ser | Ala | Asn | Val | Asp | Phe | Ala | Phe |
| | | | | 15 | | | | | 20 | | | | | 25 | |
| Ser | Leu | Tyr | Lys | His | Leu | Val | Ala | Leu | Ser | Pro | Lys | Lys | Asn | Ile | Phe |
| | | | 30 | | | | | 35 | | | | | 40 | | |
| Ile | Ser | Pro | Val | Ser | Ile | Ser | Met | Ala | Leu | Ala | Met | Leu | Ser | Leu | Gly |
| | | 45 | | | | | 50 | | | | | 55 | | | |
| Thr | Cys | Gly | His | Thr | Arg | Ala | Gln | Leu | Leu | Gln | Gly | Leu | Gly | Phe | Asn |
| | 60 | | | | | 65 | | | | | 70 | | | | |
| Leu | Thr | Glu | Arg | Ser | Glu | Thr | Glu | Ile | His | Gln | Gly | Phe | Gln | His | Leu |
| 75 | | | | | 80 | | | | | 85 | | | | | 90 |
| His | Gln | Leu | Phe | Ala | Lys | Ser | Asp | Thr | Ser | Leu | Glu | Met | Thr | Met | Gly |
| | | | | 95 | | | | | 100 | | | | | 105 | |
| Asn | Ala | Leu | Phe | Leu | Asp | Gly | Ser | Leu | Glu | Leu | Leu | Glu | Ser | Phe | Ser |
| | | | 110 | | | | | 115 | | | | | 120 | | |
| Ala | Asp | Ile | Lys | His | Tyr | Tyr | Glu | Ser | Glu | Val | Leu | Ala | Met | Asn | Phe |
| | | 125 | | | | | 130 | | | | | 135 | | | |
| Gln | Asp | Trp | Ala | Thr | Ala | Ser | Arg | Gln | Ile | Asn | Ser | Tyr | Val | Lys | Asn |
| | 140 | | | | | 145 | | | | | 150 | | | | |
| Lys | Thr | Gln | Gly | Lys | Ile | Val | Asp | Leu | Phe | Ser | Gly | Leu | Asp | Ser | Pro |
| 155 | | | | | 160 | | | | | 165 | | | | | 170 |

| | | | | | | | | | | | | | | |
|---|---|---|---|---|---|---|---|---|---|---|---|---|---|---|
| Ala | Ile | Leu | Val | Leu 175 | Val | Asn | Tyr | Ile 180 | Phe | Lys | Gly | Thr | Trp 185 | Thr |
| Gln | Pro | Phe | Asp 190 | Leu | Ala | Ser | Thr | Arg 195 | Glu | Glu | Asn | Phe | Tyr 200 | Val | Asp |
| Glu | Thr | Thr 205 | Val | Val | Lys | Val | Pro 210 | Met | Met | Leu | Gln | Ser 215 | Ser | Thr | Ile |
| Ser | Tyr 220 | Leu | His | Asp | Ser | Glu 225 | Leu | Pro | Cys | Gln | Leu 230 | Val | Gln | Met | Asn |
| Tyr 235 | Val | Gly | Asn | Gly | Thr 240 | Val | Phe | Phe | Ile | Leu 245 | Pro | Asp | Lys | Gly | Lys 250 |
| Met | Asn | Thr | Val | Ile 255 | Ala | Ala | Leu | Ser | Arg 260 | Asp | Thr | Ile | Asn | Arg 265 | Trp |
| Ser | Ala | Gly | Leu 270 | Thr | Ser | Ser | Gln | Val 275 | Asp | Leu | Tyr | Ile | Pro 280 | Lys | Val |
| Thr | Ile | Ser 285 | Gly | Val | Tyr | Asp | Leu 290 | Gly | Asp | Val | Leu | Glu 295 | Glu | Met | Gly |
| Ile | Ala 300 | Asp | Leu | Phe | Thr | Asn 305 | Gln | Ala | Asn | Phe | Ser 310 | Arg | Ile | Thr | Gln |
| Asp 315 | Ala | Gln | Leu | Lys | Ser 320 | Ser | Lys | Val | Val | His 325 | Lys | Ala | Val | Leu | Gln 330 |
| Leu | Asn | Glu | Glu | Gly 335 | Val | Asp | Thr | Ala | Gly 340 | Ser | Thr | Gly | Val | Thr 345 | Leu |
| Asn | Leu | Thr | Ser 350 | Lys | Pro | Ile | Ile | Leu 355 | Arg | Phe | Asn | Gln | Pro 360 | Phe | Ile |
| Ile | Met | Ile 365 | Phe | Asp | His | Phe | Thr 370 | Trp | Ser | Ser | Leu | Phe 375 | Leu | Ala | Arg |
| Val | Met 380 | Asn | Pro | Val | | | | | | | | | | | |

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AGGATTACCC ATGGTCGACA AGCTTAGTTA ACTCATCA    38